(12) United States Patent
Baker et al.

(10) Patent No.: US 6,225,496 B1
(45) Date of Patent: May 1, 2001

(54) PROCESS FOR THE PRODUCTION OF VINYL ACETATE UTILIZING A RECYCLE STREAM COMPRISING ACETIC ACID AND WATER

(75) Inventors: Michael James Baker, Feltham; Timothy Crispin Bristow, Beverley; Robert William Clarke, Driffield; Simon James Kitchen, Hillam; Bruce Leo Williams, Elloughton Brough, all of (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/363,391

(22) Filed: Jul. 29, 1999

(30) Foreign Application Priority Data

Aug. 11, 1998 (GB) .................................................. 9817363

(51) Int. Cl.[7] .......................... C07C 67/055; C07C 69/01
(52) U.S. Cl. .......................... 560/245; 562/545; 562/546; 560/261
(58) Field of Search .................................. 562/545, 546; 560/261, 245

(56) References Cited

U.S. PATENT DOCUMENTS

| 5,179,056 | * | 1/1993 | Bartley . |
| 5,179,057 | * | 1/1993 | Bartley . |
| 5,185,308 | * | 2/1993 | Bartley et al. . |
| 5,274,181 | * | 12/1993 | Bartley et al. . |
| 5,342,987 | * | 8/1994 | Bartley . |
| 5,990,344 | * | 11/1999 | Couves . |

FOREIGN PATENT DOCUMENTS

| 0672453 | 9/1995 | (EP) . |
| 0685449 | 12/1995 | (EP) . |
| 0685451 | 12/1995 | (EP) . |
| 0847982 | 6/1998 | (EP) . |
| 6702654 | 2/1967 | (NL) . |
| 384815 | 10/1973 | (RU) . |

* cited by examiner

*Primary Examiner*—Gary Geist
*Assistant Examiner*—Robert W. Deemie
(74) *Attorney, Agent, or Firm*—Nixon & Vanderhye

(57) ABSTRACT

Process for the production of vinyl acetate in which ethylene, acid and oxygen-containing gas are combined at elevated temperature in the presence of a catalyst material to produce (i) a product mixture comprising vinyl acetate, (ii) a liquid by-product comprising acetic acid and (iii) a gaseous by-product comprising carbon dioxide. The liquid by-product is separated from the product mixture and treated to reduce the water content therein before being recycled to the reactor such that the water entering the reactor comprises less than 6 wt %, (preferably less than 4 wt %, more preferably less than 3 wt %) of the total of acetic acid and water entering the reactor.

26 Claims, 1 Drawing Sheet

PROCESS FOR THE PRODUCTION OF VINYL ACETATE UTILIZING A RECYCLE STREAM COMPRISING ACETIC ACID AND WATER

The present invention relates to a process for the production of vinyl acetate from ethylene, acetic acid and an oxygen-containing gas in the presence of a catalyst.

BACKGROUND OF THE INVENTION

Fluid bed processes for the production of vinyl acetate from ethylene, acetic acid and an oxygen-containing gas in the presence of a fluid bed catalyst are known from, for example, EP-A-0685449, EP-A-0685451 and EP-A-0672453.

EP-A-0685449 discloses a process for manufacturing vinyl acetate in a fluid bed reactor comprising feeding ethylene and acetic acid into the fluid bed reactor through one or more inlets, feeding an oxygen-containing gas into the fluid bed reactor through at least one further inlet, co-joining the oxygen-containing gas, ethylene and acetic acid in the fluid bed reactor while in contact with a fluid bed catalyst material to enable the ethylene, acetic acid and oxygen to react to produce vinyl acetate and recovering the vinyl acetate from the fluid bed reactor.

The manufacture of vinyl acetate from ethylene, acetic acid and oxygen is an exothermic reaction and it is necessary to provide means to cool the fluidised bed reactor heat liberated. Failure to do so could lead to loss of temperature control of the reactor and eventually thermal runaway. In addition to the safety implication of thermal runaway there is the probability of catalyst damage/deactivation as a result of the high temperatures involved.

One means of cooling the system is to inject a liquid into the reaction wherein the liquid is introduced into the reactor for the purpose of removing heat therefrom by evaporation of the liquid.

Water may be used for this purpose, because water has a relatively high latent heat of evaporation. The introduction of water for this purpose, whilst effectively cooling the reaction, however, has surprisingly been found to adversely affect the selectivity to vinyl acetate product. Alternatively, the liquid acetic acid may be used to cool the system. EP-A-0847982 discloses the introduction of recycled acetic acid for this purpose. EP-A-0847982 further states that water may be present in the recycle stream as a by-product of the reaction. In practice, it is very difficult and practically inconvenient to remove all water from the acid recycle stream.

BRIEF DESCRIPTION OF THE INVENTION

We have now found that the selectivity of vinyl acetate product can be maintained at an acceptable level and the reaction system kept at the desired operating temperature by introducing recycled liquid acetic acid into the reactor wherein the recycle stream comprises a low, but effective, concentration of water.

Accordingly, the present invention provides a process for the production of vinyl acetate said process comprising:

(a) feeding ethylene, acetic acid and an oxygen-containing gas into a reactor, co-joining the ethylene, acetic acid and oxygen-containing gas at elevated temperature in the reactor in the presence of a catalyst material (i) to produce a product mixture comprising vinyl acetate, (ii) a liquid by-product comprising acetic acid and water and (iii) a gaseous by-product comprising carbon dioxide; (b) separating the liquid by-product from the product mixture; (c) treating the liquid by-product to reduce the water content therein; and (d) recycling the treated liquid by-product to the reactor in which the amount of water entering the reactor comprises less than 6 wt %, preferably less than 4 wt %, more preferably less than 3 wt % of the total of acetic acid and water entering the reactor.

The present invention solves the problem associated with the prior art by maintaining the temperature of reaction and obtaining high selectivity of vinyl acetate product by introducing water into the reactor, at relatively low levels, suitably admixed with acetic acid in the liquid by-product recycle. By the acetic acid entering the reactor is meant the total acetic acid, namely the fresh acetic acid and recycle acetic acid.

In the present invention, restricting the amount of water entering the reactor reduces the adverse effect water has been found to have on the reaction, whilst still achieving a cooling effect.

The present invention provides a process for the production of vinyl acetate from ethylene, an oxygen-containing gas and acetic acid. The ethylene may be substantially pure or may be admixed with one or more of nitrogen, methane, ethane, carbon dioxide, hydrogen and/or low levels of $C_3/C_4$ alkenes or alkanes. The ethylene in the combined feed to the reactor may be at least 60 mol %.

The oxygen-containing gas may be air or a gas richer or poorer in molecular oxygen than air. Suitably, the gas may be oxygen diluted with a suitable diluent, for example, nitrogen, argon or carbon dioxide. Preferably, the oxygen containing gas is oxygen.

The catalyst suitable for use in the process of the present invention is a Group VIII metal based catalyst on a support. Preferably, the Group VIII metal is palladium. Suitable sources of palladium include palladium (II) chloride, sodium or potassium tetrachloropalladate (II) ($Na_2PdCl_4$, or $K_2PdCl_4$), palladium acetate, $H_2PdCl_4$, palladium (II) nitrate, and palladium (II) sulphate. Suitably, the palladium concentration is at least 0.2% by weight, preferably greater than 0.5% by weight, especially about 1% based upon the total weight of catalyst. The palladium concentration may be as high as 10% by weight.

In addition to palladium, the catalyst may suitably comprise a promoter. Suitable promoters include gold, copper and/or nickel. The preferred metal is gold. Suitable sources of gold include gold chloride, tetrachloroauric acid $HAuCl_4$, $NaAuCl_4$, $KAuCl_4$, dimethyl gold acetate, barium acetoaurate or gold acetate. The preferred compound is $HAuCl_4$. The metal may be present in an amount of from 0.1 to 10% by weight in the finished catalyst.

In addition to the palladium and the promoter, the catalyst may also suitably comprise a co-promoter which is a metal selected from Group I, Group II, lanthanide or transition metals, for example cadmium, barium, potassium, sodium, iron, manganese, nickel, antimony and/or lanthanum which are present in the finished catalyst as salts, typically acetates. Generally potassium will be present. The metal may be present in a concentration of from 0.1 to 15%, preferably 1 to 5% by weight of metal in the finished catalyst. Suitably, the catalyst may comprise up to 15% by weight co-promoter. Where the process is carried out in a fixed bed reactor, it is preferred to have a co-promoter concentration of 3 to 11% by weight. Where the process is carried out in a fluid bed reactor, and especially with liquid acetic acid, the preferred concentration of co-promoter is up to 6% by weight, especially 2.5 to 5.5% by weight where a liquid acetic acid feed is used. Where the acid is introduced in the vapour phase the co-promoter may be present in a concentration up to 11 wt %.

The catalyst is a supported catalyst. Suitable supports include porous silica, alumina, silica/alumina, silica/titania, titania, zirconia or carbon. Preferably, the support is silica. Suitably, the support may have a pore volume from 0.2 to 3.5 mL per gram of support, a surface area of 5 to 800 $m^2$ per gram of support and an apparent bulk density of 0.3 to 1.5 g/mL. For fluid bed operation, the support may typically have a particle size distribution such that at least 60% of the catalyst particles have a particular diameter of below 200 microns. Preferably, at least 50%, more preferably at least 80% and most preferably at least 90% of the catalyst particles have a particular diameter of less than 105 microns. Preferably no more than 40% of the catalyst particles have a diameter of less than 40 microns.

The catalyst may suitably be prepared according to the method described in detail in EP-A-0672453. Suitably, the first stage of the catalyst preparation process involves impregnation of the support material with a solution containing the required Group VIII metal and the promoter metal in the form of soluble salts. Examples of such salts are soluble halide derivatives. The impregnating solution is preferably an aqueous solution and the volume of solution used is such that it corresponds to between 50 and 100% of the pore volume of the support, preferably 50 to 99% of the pore volume.

The impregnated support is then dried at ambient or reduced pressure and from ambient temperature to 150° C., preferably 60 to 130° C. prior to metals reduction. To convert such materials into the metallic state, the impregnated support is treated with a reducing agent such as ethylene, hydrazine or, formaldehyde or hydrogen. If hydrogen is used, it will usually be necessary to heat the catalyst to 100 to 850° C. in order to effect complete reduction.

After the steps described above have been carried out, the reduced catalyst is washed with water and then dried. The dried carrier is then impregnated with the required amount of co-promoter and thereafter dried. Alternatively, the wet, reduced, washed material is impregnated with co-promoter then dried.

The method of catalyst preparation may be varied to optimise catalyst performance based on maximising vinyl acetate yield and selectivity.

The process of the present invention requires the step of reducing the water content in the liquid by-product stream and returning this treated stream back to the reactor.

The water content in the liquid by-product stream may be reduced by various methods. Suitably, the water may be reduced by passing the liquid by-product stream through a distillation column and recovering an acetic acid/water mixture from the base of the distillation column. The number of plates within the column may be selected according to the desired reduction in water concentration. The acetic acid/water mixture may be withdrawn from the base of the distillation column either in the liquid or vapour form. An advantage of taking the acetic acid/water mixture distillation product as a vapour is that it can have lower contamination with corrosion metal and/or other heavies than a liquid product which has less potential to poison the catalyst. As regards the vapour product, this may be further treated to reduce further the water concentration by partial condensation. In this embodiment, the total column vapour at the base of the distillation column is passed through a condenser which effects condensation of only a portion of the vapour introduced thereto. The uncondensed vapour then passes up the distillation column whilst the condensate is collected and recycled to the reactor. Preferably, the partial condenser may be located within the distillation column, but may also be located outside in ducts. An advantage of using partial condensation is that it produces an acetic acid/water mixture product from the distillation column which has a lower water concentration than would be achieved by withdrawing or segregating a portion of the distillation column vapour and condensing it. To achieve the required water concentration in the vapour product from the base of the distillation column with the latter approach (total condensation of a portion of the column vapour) the distillation column would have to operate with a low water concentration, which could present operational difficulties. Typically, partial condensation may reduce the water content in the by-product acid/water stream to as low as 5 wt %. The water content thus in the acid stream entering the reactor will then be less than this value.

The water content of the liquid by-product stream may also be reduced by chemical means, such as reaction with acetic anhydride.

The treated acid/water recycle stream may be introduced into the reactor either separately and independent of the feed acetic acid. Alternatively, the recycle stream may be mixed with the fresh acetic acid prior to introduction into the reactor. The introduction to the reactor of fresh acetic acid (which contains little water) is beneficial in limiting the amount of water fed to the reactor. This is preferable to using the fresh acetic acid in other parts of the process such as in the absorber. The two streams or a combined stream may be introduced into the reactor by a variety of different methods including the fluid bed reactor grid, sparge bars and liquid/gas feed nozzles. The acetic acid containing stream or streams is preferably introduced through an atomising nozzle in which a gas is used to assist in the atomisation of the liquid. Alternatively, liquid-only spray nozzles may be used. The ethylene and oxygen-containing gas may be introduced through separate inlets. Suitable nozzles for use in the present invention are disclosed in WO-A-94/28032.

Preparation of vinyl acetate using the process of the present invention is typically carried out by contacting ethylene, acetic acid and an oxygen-containing gas with the catalyst at a temperature of from 100 to 400° C. preferably 140 to 210° C. and a pressure of from $10^5$ Pa gauge to $2 \times 10^6$ Pa gauge (1 to 20 barg), preferably from $6 \times 10^5$ Pa gauge to $1.5 \times 10^6$ Pa gauge (6 to 15 barg).

The process of the present invention may be carried out in a fixed bed reactor or fluid bed reactor. Preferably a fluid bed reactor is used with a fluid bed catalyst.

BRIEF DESCRIPTION OF THE DRAWING

The process of the present invention will now be illustrated with reference to FIG. 1 and the following experiments wherein.

DETAILED DESCRIPTION OF PREFFERRED EMBODIMENTS

Figure 1:
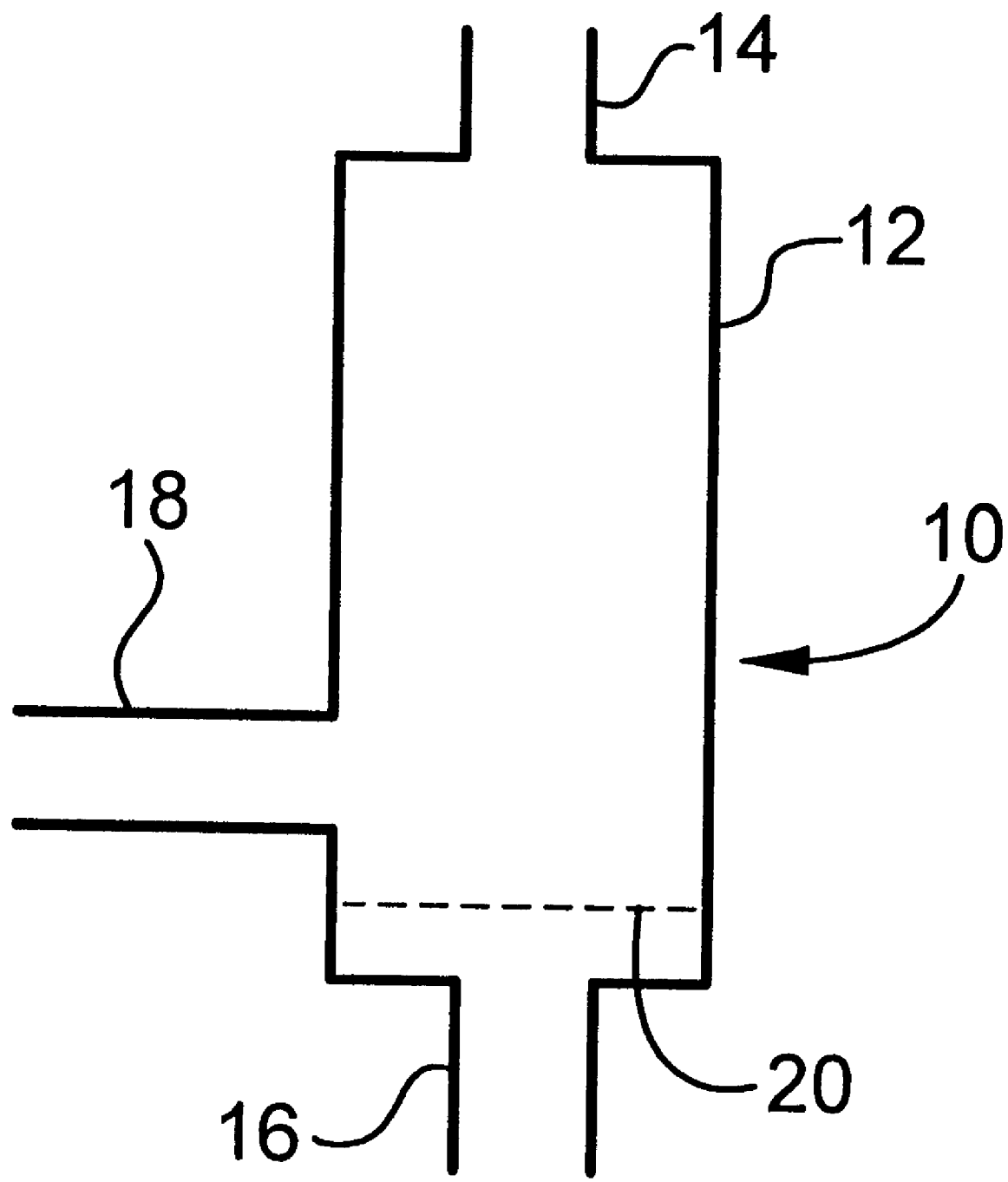
FIG. 1 is a schematic diagram of a fluid bed reactor used in the process of the present invention.

Refering to FIG 1. The reactor has a 0.0381 m (1.5 inch) diameter equipped with two feed inlets. The reactor (10) defines a tubular housing (12) having an outlet (14) and first (16) and second (18) inlets. The reactor (10) further comprises a sintered grid plate (20) positioned within housing (12).

In operation, the reactor (10) is charged with 300 g of a fluid bed catalyst to form a fluid bed. Feed comprising ethylene, nitrogen, oxygen, vapourised acetic acid and vapourised water are introduced into the reactor (10) via the first inlet (16). Oxygen and/or nitrogen is introduced into the reactor (10) via the second inlet (18).

In these experiments the acetic acid and water are introduced to the reactor as vapours rather than liquids. The experiments thus illustrate the effect of water on the reaction. It is expected that introduction of the acetic acid and water as liquids would effect cooling according to the process of the present invention.

Experiments 1, 2 and 3 are experiments wherein the acetic acid stream comprises less than 6% by weight water. Experiment A is not according to the present invention in that the stream comprises greater than 6% water.

Preparation of Catalyst Support

The support used for all catalyst preparations was prepared by spray-drying a mixture of silica sol 1060 (obtained from Nalco Chemical Company) and Aerosil® silica (obtained from Degussa Chemical Company). In the dried support, 80% of the silica came from the sol and 20% of the silica came from the Aerosil. The spray-dried microspheres were calcined in air at 640° C. for 4 hours. The particle size distribution of the support which was used for the catalyst preparations is as follows:

| Particle size | % |
| --- | --- |
| >300 microns | 2 |
| 44–300 microns | 68 |
| <44 microns | 30 |

It should be understood that the particle size distribution given above is not intended to be limiting and that variations in this distribution are contemplated depending upon reactor size and operating conditions.

Preparation of Catalyst

Silica support (54.4 kg) was impregnated with a solution of $Na_2PdCl_4 \cdot xH_2O$ (containing 1000 g Pd) and $HAuCl_4 \cdot xH_2O$ (containing 400 g Au) in distilled $H_2O$ by incipient wetness. The resulting mixture was mixed thoroughly, left to stand for 1 hour and dried overnight.

A portion of the impregnated material (18 kg) was added slowly to a 5% solution of $N_2H_4$ in distilled $H_2O$ and the mixture allowed to stand with occasional stirring. Thereafter the mixture was filtered and washed with 4×400 litres distilled $H_2O$. The solid was then dried overnight.

The material was impregnated with an aqueous solution of KOAc (1.3 kg) by incipient wetness. The resulting mixture was mixed thoroughly, left to stand one hour and dried overnight. The resulting catalyst composition was 1.63 wt % Pd, 0.67 wt % Au, 6.4 wt % KOAc.

Experiment 1

A fluidised bed reactor as shown in FIG. 1 was used for the process. The reactor is equipped with two feed inlets. Oxygen and nitrogen are fed through the second inlet whilst ethylene, nitrogen, oxygen, crude vapourised acetic acid admixed with vapourised recycled acetic acid and (vapourised water when used) are fed through the first inlet. The feed consisted of ethylene (330 g/hr), acetic acid (255 g/hr), oxygen (83.3 ghr). Nitrogen is as indicated in Table 1. The reactor was charged with 300 g of fluid bed catalyst prepared as described above. The acid stream contained no water.

Inlet gas flows were regulated by mass flow controllers; liquids were fed using a pump. The reactor pressure was maintained at 8 barg. The reactor temperature was maintained at 152° C. and all lines leading to and from the reactor were heat traced and maintained at 160° C. in order to prevent condensation of feeds or products.

The gaseous reactor effluent was analysed on-line using a Chrompack Model CP9000 gas chromatograph equipped with both FID and TCD detectors. Ethylene and carbon dioxide were separated on a Poraplot U column and quantified by TCD, oxygen and nitrogen were separated on a molecular sieve column and quantified by TCD; and vinyl acetate and acetic acid and other by-products were separated on a DB1701 capillary column and quantified with the FID. Data were analysed via a customised Excel spreadsheet.

The results are given in Table 1.

Experiment 2

The procedure of experiment 1 was repeated with a water content of 3.1 wt % in the acid stream. The results are given in Table 1.

Experiment 3

The procedure of experiment 1 was repeated with a water content of 5.1 wt % in the acid stream. The results are given in Table 1.

Experiment A

The procedure of experiment 1 was repeated with a water content of 7.4 wt % in the acid stream. The results are given in Table 1.

The results shown in Table 1 indicate that selectivity is improved as water concentration decreases, especially below 6 wt %. It should be noted that the greatest selectivity is obtained where water is absent from the feed system. In a large scale commercial plant, this is possible but unlikely because the costs involved in removing all of the water in the by-product stream would be prohibitive. Thus, the commercial operating conditions comprise water but this level is kept to less than 6 wt % in the combined acid stream. By introducing the acetic acid containing less than 6 wt % water as a liquid the reactor would be cooled.

TABLE 1

| Experiment | Weight % water in acid | g/hr water in feed | g/h Nitrogen in feed | g/hr VA/hr in product | g $CO_2$/hr in product | gVA/kg cat/hr | % VA selectivity* |
|---|---|---|---|---|---|---|---|
| 1 | 0 | 0 | 326 | 134 | 18.3 | 445 | 88.2 |
| 2 | 3.1 | 8.1 | 321 | 135 | 19.4 | 450 | 87.7 |
| 3 | 5.1 | 13.6 | 309 | 131 | 20.1 | 436 | 87.0 |
| A | 7.4 | 20.3 | 295 | 125 | 20.8 | 416 | 86.0 |

*Calculated as VA/(VA + 0.5 $CO_2$)

We claim:

1. A process for the production of vinyl acetate, said process comprising:
   (a) feeding ethylene, acetic acid and an oxygen-containing gas into a reactor, co-joining the ethylene, acetic acid and oxygen-containing gas at elevated temperature in the reactor in the presence of a catalyst material to produce (i) a product mixture comprising vinyl acetate, (ii) a liquid by-product comprising acetic acid and water and (iii) a gaseous by-product comprising carbon dioxide;
   (b) separating the liquid by-product from the product mixture;
   (c) treating the liquid by-product to reduce the water content therein; and
   (d) recycling the treated liquid by-product to the reactor in which the amount of water entering the reactor comprises less than 6 wt %, of the total of acetic acid and water entering the reactor.

2. A process as claimed in claim 1 in which the water content of said liquid by-product is reduced by passing said liquid by-product through a distillation column and removing from the base of said distillation column a distillation product having reduced water concentration.

3. A process as claimed in claim 2 in which said distillation product having a reduced water concentration is removed from the base of said distillation column as a vapour.

4. A process as claimed in claim 3 in which the total vapour flow at the base of the distillation column is passed through a partial condenser and a distillation product having a reduced water concentration is collected as condensate therefrom.

5. A process as claimed in claim 4 in which said distillation product has a water concentration of about 5% by weight.

6. A process as claimed in claim 4 in which said partial condenser is located within said distillation column.

7. A process as claimed in claim 1 in which the water content of said liquid by-product is reduced by chemical reaction.

8. A process as claimed in claim 7 in which said chemical reaction is with acetic anhydride.

9. A process as claimed in claim 1 in which said treated acetic acid/water liquid by-product having reduced water concentration is mixed with fresh acetic acid prior to introduction into said reactor.

10. A process as claimed in claim 3 in which said treated acetic acid/water liquid by-product having reduced water concentration is mixed with fresh acetic acid prior to introduction into said reactor.

11. A process as claimed in claim 4 in which said treated acetic acid/water liquid by-product having reduced water concentration is mixed with fresh acetic acid prior to introduction into said reactor.

12. A process as claimed in claim 5 in which said treated acetic acid/water liquid by-product having reduced water concentration is mixed with fresh acetic acid prior to introduction into said reactor.

13. A process as claimed in claim 1 in which said catalyst material comprises a Group VIII metal, and a promoter selected from the group consisting of gold, copper, nickel and mixtures thereof.

14. A process as claimed in claim 13 in which said catalyst material additionally comprises a co-promoter selected from the group consisting of Group I, Group II, lanthanide and transition metals.

15. A process as claimed in claim 1 in which said reactor comprises a fluid bed reactor.

16. A process as claimed in claim 3 in which said reactor comprises a fluid bed reactor.

17. A process as claimed in claim 4 in which said reactor comprises a fluid bed reactor.

18. A process as claimed in claim 5 in which said reactor comprises a fluid bed reactor.

19. A process as claimed in claim 9 in which said reactor comprises a fluid bed reactor.

20. A process as claimed in claim 13 in which said reactor comprises a fluid bed reactor.

21. A process as claimed in claim 14 in which said reactor comprises a fluid bed reactor.

22. A process as claimed in claim 1 in which the amount of water entering the reactor comprises less than 4 wt % of the total of acetic acid and water entering the reactor.

23. A process as claimed in claim 1 in which the amount of water entering the reactor comprises less than 3 wt % of the total of acetic acid and water entering the reactor.

24. A process as claimed in claim 15 in which the amount of water entering the reactor comprises less than 4 wt % of the total of acetic acid and water entering the reactor.

25. A process as claimed in claim 15 in which the amount of water entering the reactor comprises less than 3 wt % of the total of acetic acid and water entering the reactor.

26. A process as claimed in claim 13 wherein the Group VIII metal is palladium.

* * * * *